United States Patent
Wadman et al.

(10) Patent No.: US 10,752,602 B2
(45) Date of Patent: Aug. 25, 2020

(54) PROCESS FOR THE PRODUCTION OF 1,4-BUTANEDIOL AND TETRAHYDROFURAN FROM FURAN

(71) Applicant: SHELL OIL COMPANY, Houston, TX (US)

(72) Inventors: Sipke Hidde Wadman, Amsterdam (NL); Jean Paul Andre Marie Joseph Ghislain Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 15/758,626

(22) PCT Filed: Sep. 8, 2016

(86) PCT No.: PCT/EP2016/071221
§ 371 (c)(1),
(2) Date: Mar. 8, 2018

(87) PCT Pub. No.: WO2017/042289
PCT Pub. Date: Mar. 16, 2017

(65) Prior Publication Data
US 2018/0251438 A1    Sep. 6, 2018

(30) Foreign Application Priority Data

Sep. 10, 2015   (EP) .................................... 15184742

(51) Int. Cl.
C07D 307/08      (2006.01)
C07C 29/17       (2006.01)
(52) U.S. Cl.
CPC .......... *C07D 307/08* (2013.01); *C07C 29/172* (2013.01)
(58) Field of Classification Search
CPC .................................................... C07D 307/08
USPC ........................................................ 549/429
See application file for complete search history.

(56) References Cited

U.S. PATENT DOCUMENTS

| | | |
|---|---|---|
| 4,146,741 A | 3/1979 | Prichard |
| 5,905,159 A | 5/1999 | Fischer et al. |
| 2017/0320842 A1 | 11/2017 | Lange et al. |
| 2017/0349515 A1 | 12/2017 | Lange et al. |

FOREIGN PATENT DOCUMENTS

| | | |
|---|---|---|
| WO | 0222593 A1 | 3/2002 |
| WO | 2012041990 A1 | 4/2012 |
| WO | 2014191504 A1 | 12/2014 |
| WO | WO 2014/191522 A1 * | 12/2014 |

OTHER PUBLICATIONS

Hoydonck et al., "Furfural and Derivatives", Ulmann's Encyclopedia of Industrial Chemistry, vol. 16, 2012, pp. 285-313.
Dunlop et al., "The Furans", Reinhold Publ. Co., ACS Monograph Series, 1953, 4 pages.
Zeitsch, "The Chemistry and Technology of Furfural and its Many By-Products", Sugar Series 13, Elsevier, 2000, 20 pages.
Lange et al., "Furfural—A Promising Platform for Lignocellulosic Biofuels", ChemSusChem, vol. 5, No. 1, Jan. 9, 2012, pp. 150-166, XP055338725.
Watson. "Butane-1,4-diol from Hydrolytic Reduction of Furan", Ind. Eng. Chem. Prod. Res. Dev., vol. 12, No. 4, Dec. 1973, pp. 310-311.
Pan et al., "Catalytic Conversion of Furfural into a 2,5-Furandicarboxylic Acid-Based Polyester with Total Carbon Utilisation", ChemSusChem, vol. 6, Issue No. 1, Jan. 2013, pp. 47-50, XP055206669.
International Search Report and Written Opinion received for PCT Patent Application No. PCT/EP2016/071221, dated Oct. 14, 2016, 8 pages.

* cited by examiner

*Primary Examiner* — Taofiq A Solola

(57) ABSTRACT

The present invention provides a process for the production of 1,4-BDO and THF from furan, said process comprising: (i) contacting furan with hydrogen and water in a reactor in the presence of a catalytic composition, wherein the furan and water are contacted in the presence of a solvent, said solvent being selected from one or more of THF, 1,4-BDO and NBA, and converting at least a portion of said furan to 1,4-BDO and THF; (ii) producing a reactor product stream comprising gases, water, THF, 1,4-BDO and furan; (iii) separating gases from the reactor product stream; (iv) then separating at least a portion of each of the THF and 1,4-BDO from said reactor product stream; and (v) recycling the remainder of the reactor product stream, comprising water, optionally furan, and at least one of THF, 1,4-BDO and NBA, to the reactor.

7 Claims, 1 Drawing Sheet

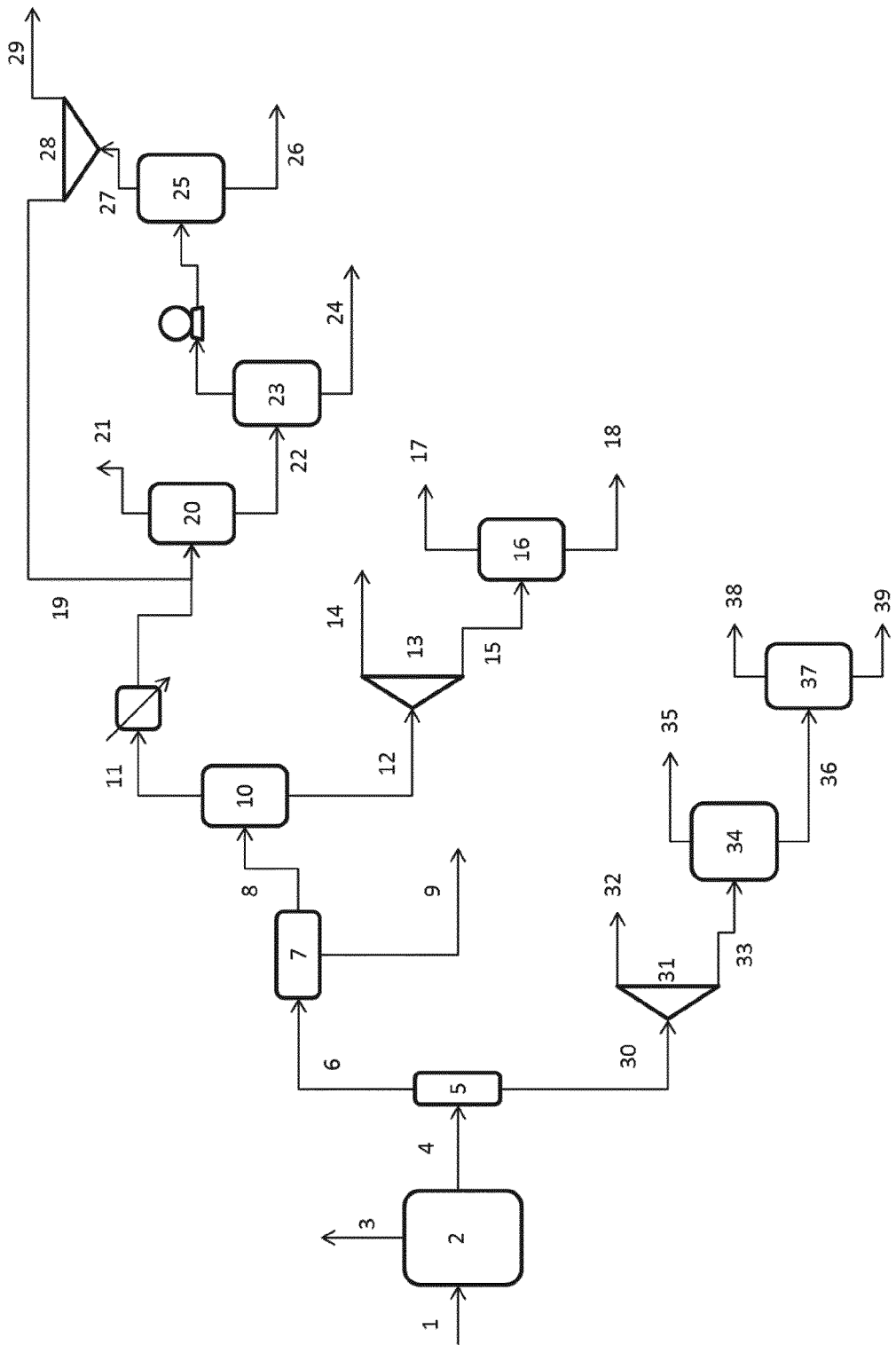

PROCESS FOR THE PRODUCTION OF 1,4-BUTANEDIOL AND TETRAHYDROFURAN FROM FURAN

PRIORITY CLAIM

The present application is the National Stage (§ 371) of International Application No. PCT/EP2016/071221, filed 8 Sep. 2016, which claims priority from European Application No. 15184742.3, filed 10 Sep. 2015 incorporated herein by reference.

FIELD OF THE INVENTION

The present invention relates a process for the production of 1,4-butanediol and tetrahydrofuran from furan.

BACKGROUND OF THE INVENTION

Furan and its derivatives are useful precursors for industrial chemicals in the area of, for example, pharmaceuticals, herbicides and polymers. Furan may be converted into tetrahydrofuran (THF) and 1,4-butanediol (1,4-BDO). THF and 1,4-BDO are valuable chemicals used industrially as solvents and in the production of elastic fibres such as elastane/spandex, polybutyrate terephthalate and derivatives of gamma butyrolactone (GBL).

These chemicals are usually produced industrially via a number of routes from petrochemical feedstocks, obtainable from fossil fuels. In recent years, increased efforts have focused on producing chemicals, including 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H E; Van Rhijn, W M; Van Rhijn, W; De Vos, D E; & Jacobs, P A; (2012) Furfural and Derivatives, in Ullmann's Encyclopedia of Industrial Chemistry (volume 16, pp 285-313), Wiley-VCH Verlag GmBH & Co. KGaA, Weinheim; Dunlop, A P; and Peters, F N; in The Furans Reinhold Publ. Co, 1953; K. J. Zeitsch, in "The Chemistry and Technology of Furfural and its Many By-products" Sugar Series 13, Elsevier, 2000; Lange, J-P; van der Heide, E; van Buijtenen, J; and Price, R; Furfural—A Promising Platform for Lignocellulosic Biofuels; ChemSusChem 2012, 5, 150-166 and Watson, J. M.; Ind. Eng. Chem. Prod. Res. Develop., 1973, 12(4), 310. Furfural may be obtained from hemicellulose via acid hydrolysis in the liquid phase as well as in the gas phase as described in WO2002022593 and WO2012041990.

The conversion of furan to THF and 1,4-BDO by hydrogenation in the presence of water, acetic acid and Raney nickel or oxide supported nickel catalyst is described in Watson, J M; Ind. Eng. Chem. Prod. Res. Develop., 1973, 12(4), 310.

A process for the conversion of furan into 1,4-BDO and THF is taught in U.S. Pat. No. 5,905,159. This document teaches a process in which furan is converted as a reaction mixture with water and in the presence of hydrogen but in the absence of a water-soluble acid in a single stage over a hydrogenation catalyst. The hydrogenation catalyst of U.S. Pat. No. 5,905,159 contains at least one element of subgroup I, V, VI, VII or VIII in the form of a compound or in elemental form, with the restriction that the catalyst does not contain nickel alone being applicable. The preferred catalyst in this process is Re/Ru on active carbon. A similar catalyst is used in the process described in Pan, T; Deng, J; Xu, Q; Zuo, Y; Guo, Q-X and Fu, Y; Catalytic Conversion of Furfural into a 2,5-Furandicarboxylic Acid-based Polyester with Total Carbon Utilisation; ChemSusChem 2013, 6, 47-50.

As well as THF and 1,4-BDO, other useful products such as n-butyl alcohol (NBA) and GBL may be produced in such hydrogenation processes.

More effective catalysts for the conversion of furan into 1,4-BDO and THF are taught in co-pending applications EP14196391.8, said catalysts incorporating rhenium and palladium on solid supports and EP14199023.4, said catalyst incorporating one or more metals from those in group 8, 9, 10 and 11 of the periodic table supported on amorphous or crystalline aluminosilicate supports.

In the reductive hydration of furan wherein 1,4-BDO is a desired product, furan and water need to be reacted in the presence of hydrogen and the catalyst. For such a process to proceed effectively, the water and furan are preferably in the same liquid phase. It is also preferred to use an excess of water to furan in this reaction in order to increase the selectivity to 1,4-BDO over THF. The majority of this water may be separated and recycled after removal of the reaction products. However, the solubility of furan in water and water in furan is too low and prevents a single liquid phase to be formed at concentrations suitable for a commercial process.

Further, separation of 1,4-BDO, THF and NBA in an efficient manner from an aqueous product stream provides an on-going challenge.

It is, therefore, an object of the present invention to provide a process for the production of 1,4-BDO from furan, which overcomes these problems associated with the solubility of furan in water (and vice versa) and the separation of the reaction products and provides an efficient and effective process.

SUMMARY OF THE INVENTION

Accordingly, the present invention provides a process for the production of 1,4-BDO and THF from furan, said process comprising:
(i) contacting furan with hydrogen and water in a reactor in the presence of a catalytic composition, wherein the furan and water are contacted in the presence of a solvent, said solvent being selected from one or more of THF, 1,4-BDO and NBA, and converting at least a portion of said furan to 1,4-BDO and THF;
(ii) producing a reactor product stream comprising gases, water, THF, 1,4-BDO and furan;
(iii) separating gases from the reactor product stream;
(iv) then separating at least a portion of each of the THF and 1,4-BDO from said reactor product stream; and
(v) recycling the remainder of the reactor product stream, comprising water, optionally furan, and at least one of THF, 1,4-BDO and NBA, to the reactor.

BRIEF DESCRIPTION OF THE DRAWINGS

FIG. 1 is a schematic diagram of an exemplary, but non-limiting, embodiment of the process as described herein.

DETAILED DESCRIPTION OF THE INVENTION

The present inventors have found that a process for the production of 1,4-BDO and THF from furan in which furan is reacted with hydrogen and water in the presence of a catalytic composition, may be improved by carrying out said reaction in the presence of a solvent selected from one or more of 1,4-BDO, THF and NBA. Such a process provides a number of advantages over known processes in the art. These solvents and mixtures thereof provide a single liquid phase comprising the solvent, furan and water under the conditions used in the reactor. Further, there is no requirement for complete separation of the solvent used. Only roughly the amount of each of NBA (if present), 1,4-BDO and THF produced in the reactor needs to be isolated with the remaining amount recycled as solvent. This reduces the overall distillation duty and complexity of the scheme required in the purification of the desired products. The process and other advantages are described in greater detail below.

In the process, furan is contacted with hydrogen and water in a reactor. The molar ratio of furan:water provided to the reactor is preferably in the range of from 1:1 to 1:20, more preferably in the range of from 1:1.5 to 1:10.

Suitable conditions in the reactor include a temperature of at least 100° C., preferably at least 120° C., more preferably at least 140° C. and at most 350° C., preferably at most 250° C., more preferably at most 200° C. The pressure in the reactor is suitably at least 0.1 MPa, preferably at least 1 MPa more preferably at least 3 MPa and suitably at most 15 MPa, preferably at most 10 MPa and more preferably at most 7 MPa. Preferably, the hydrogen is present in an amount such that the $H_2$:furan molar ratio is in the range of from 0.2:1 to 100:1, preferably in the range of from 1:1 to 10:1, most preferably 2:1 to 5:1.

The catalytic composition used in the process of the present invention preferably contains at least one metal selected from the group consisting of Fe, Ru, Os, Co, Rh, Ir, Ni, Pd, Pt on a solid support. The at least one metal may be present on the catalytic composition in its elemental form or as compounds.

Further to the above-mentioned metal or metals, the catalytic composition used in the present invention may contain one or more additional metals, for example promotor metal or metals that will at least in part catalyse different reactions, such as ring-opening. A suitable example of such an additional metal is rhenium.

The total amount of said metal or metals (considered as elements) including the additional metal or metals, if present on the catalytic composition may vary within wide ranges, and may be of from 0.01 to 20 wt %, 0.1 to 10 wt % or 0.5 to 5 wt % on the basis of the total weight of the catalytic composition. Preferably, the total amount of said metal or metals is at least 0.01 wt %, more preferably at least 0.02 wt %, more preferably at least 0.03 wt %, more preferably at least 0.1 wt %, more preferably at least 0.3 wt %, most preferably at least 1.0 wt %. Further, preferably, the total amount of said metal or metals is at most 20 wt %, more preferably at most 15 wt %, most preferably at most 10 wt %.

Suitable supports in the present invention include oxides of aluminium, titanium, zirconium, silicon, as such or in combination with other oxides. The support can be amorphous or crystalline, including clays such as montmorillonite or zeolites, such as ZSM-5 or ZSM-10 zeolites. In another embodiment, the support is composed of carbon such as active carbon or carbon fibres. Mixtures of different supports can, of course, also serve as supports for the catalytic compositions to be used in the process of the invention. Preferred supports are titanium oxides, zirconium dioxide and active carbon. More preferred are zirconium dioxide and active carbon. Most preferably, the support is active carbon.

Any suitable reactor may be used for the production of 1,4-BDO and THF from furan. These include, but are not limited to fixed bed and slurry reactors.

The solvent used in the process of the present invention is selected from one or more of THF, 1,4-BDO and NBA. Mixtures of more than one of THF, 1,4-BDO and NBA are particularly preferred.

Within the reactor at least a portion of the furan is converted to 1,4-BDO and THF. Preferably, at least 50 wt %, more preferably at least 70 wt %, even more preferably at least 90 wt %, most preferably at least 98 wt % of the furan is consumed in the reaction. As well as 1,4-BDO and THF, other desirable materials and by-products will be formed. These include, but are not limited to, NBA and GBL.

The reaction will produce a reactor product stream with is withdrawn from the reactor. Said reactor product stream will comprise gases, water, THF, 1,4-BDO and, optionally, NBA. Other by-products will also be present in the reactor product stream.

The reactor product stream is then treated to remove gases, particularly hydrogen, from said stream. This may be carried out by any suitable gas/liquid separation process. A preferred method involves spontaneous gas/liquid separation in a vessel, optionally in multiple stages that are operating at different temperatures and pressures. One exemplary embodiment may involve a sequence of hot high pressure, cold high pressure, hot low pressure and cold low pressure gas/liquid separations. The gases may then, optionally, be recycled to the reactor.

After gases have been removed, the reactor product stream is treated in order to remove and isolate at least a portion of each of the THF, 1,4-BDO and NBA (if present) present in said reactor product stream. Any remaining amount of each of THF, 1,4-BDO and NBA present may then be recycled and re-used as solvent in the reaction.

Preferably, the amount of each of the THF, 1,4-BDO and NBA separated from the reactor product stream and isolated is at least 90 wt %, more preferably at least 100 wt %, even more preferably at least 110 wt % of the amount produced in the reaction of the furan with $H_2$ and water. Suitably, the amount of each of the THF and 1,4-BDO separated from the reactor product stream and isolated is no more than 150 wt % of the amount produced in the reaction of the furan with $H_2$ and water. Suitably, the amount of NBA separated from the reactor product stream and isolated is no more than 300 wt % of the amount produced in the reaction of the furan with $H_2$ and water. If any of the THF, 1,4-BDO and NBA produced in the reaction of the furan with $H_2$ and water remains after separation, it may suitably be recycled with the solvent and water without degradation of the materials.

Alternatively, if more than the amount of any of NBA, THF and 1,4-BDO produced in the reactor is separated and isolated, then further NBA, THF and/or 1,4-BDO may be provided to the reactor as solvent to make up the balance. Such make up solvent may be obtained from the isolated products of the process or may be obtained elsewhere.

The remainder of the reactor product stream, comprising water and at least one of THF, 1,4-BDO and NBA may then be recycled to the reactor. Suitably this recycle stream should contain enough solvent for the reaction. As indicated above, fresh solvent may be added if required to make up for amounts that have been separated and purified and any other losses or purges incurred throughout the process. Additional water may also be added. Further, a purge stream may be taken from the recycle stream in order to prevent build-up of undesirable by-products.

In one preferred embodiment of the invention, the solvent comprises 1,4-BDO. In this embodiment, an initial distillation of the reaction product stream after removal of gases, provides a bottoms stream comprising 1,4-BDO and water. This embodiment has the advantage that, as only a portion of the 1,4-BDO in this bottoms stream needs to be isolated, a portion of this stream may be recycled directly to the reactor. Therefore, only a portion of the water present will need to be distilled off the 1,4-BDO, thus reducing the distillation duty required.

In another preferred embodiment of the invention, the solvent comprises NBA. As NBA is only produced in relatively small quantities in the reactor, this embodiment has the advantage that only a small amount of the total amount of NBA present in the reactor product stream needs to be isolated and purified from said reactor product stream which contains a large amount of NBA as solvent. This simplifies the isolation and purification of NBA.

Further, in this embodiment, after separation of the BDO and once the resultant stream has been condensed, a phase separation will may occur between an organic-rich liquid phase containing the NBA and other organic materials, and a water-rich liquid phase, depending on the ratio of NBA to water and temperature. This will allow facile liquid/liquid separation of at least a portion of the water, which can then be recycled to the reactor without incurring any further distillation duty. Suitable ratios may be determined by the skilled person. Such a split can be seen, for example, at a temperature of 50° C. in an NBA/water mixture containing in the range of from 6 to 77 wt % NBA, or at a temperature of 80° C. in an NBA/water mixture containing in the range of from 7 to 73 wt % NBA.

In a further preferred embodiment of the invention, the solvent comprises THF. A liquid/liquid separation may also occur in this embodiment, after separation of the BDO and once cooled below the reactor temperature, depending on the ratio of THF to water. This will allow facile liquid/liquid separation of at least a portion of the water, which can then be recycled to the reactor without incurring any further distillation duty. Suitable ratios of THF/water may readily be determined by the skilled person. Such a split can be seen, for example, at a temperature of 125° C. in a THF/water mixture containing in the range of from 31 to 66 wt % THF, or at a temperature of 80° C. in a THF/water mixture containing in the range of from 35 to 70 wt % THF.

In a particularly advantageous embodiment, the solvent comprises NBA and 1,4-BDO. In this embodiment of the invention, the weight ratio of NBA:1,4-BDO is preferably in the range of from 1:5 to 1:0.2, more preferably in the range of from 1:2 to 1:0.5. Most preferably, in this embodiment, the weight ratio of NBA:1,4-BDO is approximately 1:1.

In a further particularly advantageous embodiment, the solvent comprises NBA, 1,4-BDO and THF. Many ratios of the three materials may suitably be used in this embodiment of the invention. Preferably, the solvent comprises no more than 70 wt %, more preferably no more than 50 wt % of each of NBA, 1,4-BDO and THF. Further, also preferably, the mixture comprises at least 10 wt %, more preferably at least 20 wt % of each of NBA, 1,4-BDO and THF

DETAILED DESCRIPTION OF THE DRAWINGS

FIG. 1 shows an exemplary embodiment of a purification and isolation set up suitable for use when the solvent comprises NBA, 1,4-BDO and water.

In this embodiment, a reactor process stream 1 from a process in which furan is reacted with hydrogen and water in a reactor in the presence of a catalytic composition in the presence of a solvent, is provided to gas/liquid separator 2.

A gaseous stream 3 is removed and the resultant liquid stream 4 is provided to column 5. The liquid stream 4 is distilled to provide an overhead stream 6 comprising THF, NBA, any furan present and water and a bottoms stream 30 comprising BDO, water and some NBA.

The overhead stream 6 is subjected to separation in liquid/liquid separator 7 to give an aqueous stream 9, which contains few organics and can be recycled and an organics stream 8, which contains the THF, NBA, and any remaining furan. This stream will also contain water. Further distillation is carried out in column 10 to produce a bottoms stream 12 comprising water and NBA and an overheads stream 11 comprising water and THF as well as any furan present. The skilled person will recognise that water and THF will form an azeotrope under conditions suitable for the described separations.

The bottoms stream 12 may optionally contain a liquid/liquid separator to further separate the NBA and water present therein. If such a separator is present it may be additional to or instead of liquid/liquid separator 7.

The bottom stream 12 is then split in splitter 13 with a portion 14 of the stream recycled to the reactor. A further portion 15 of the stream is then provided to column 16 to produce a pure NBA bottom stream 18 and a water/NBA top stream 17. This water/NBA stream may also contain THF and can be recycled to the reactor.

Stream 11 is provided to column 20 and overhead stream 21 is produced that contains some furan and can be recycled. A wet THF stream 22 is produced as the bottoms stream for this column 20. A two stage distillation is carried out on the wet THF stream 22 over two columns 23 and 25. Column 23 is operated at a lower pressure (1 bar, for example) and column 25 is operated at a higher pressure (12 bar, for example). This process takes advantage of the different compositions of the THF/water azeotrope at different pressures to produce a dry THF stream 26. Aqueous stream 24 can be recycled to the reactor. This stream may contain some NBA. The water-azeotrope produced as overheads stream 27 may be split with a portion recycled to the distillation system and a portion recycled to the reactor. Such a split can be controlled to provide the optimum ratio of water:THF in the distillation system to isolate the required amount of THF at the required purity.

Bottoms stream 30, from column 5 is split in splitter 31 and a portion of this stream is recycled to the reactor. The remaining portion 33 of the stream is provided to column 34, wherein water and NBA are removed as an overheads stream 35. This overhead stream may be recycled to the reactor. The remaining stream 36 is subjected to distillation in column 37 to provide a pure BDO stream 38 and a stream comprising any heavies present in the system 39.

The invention will now be illustrated by the following non-limiting example.

Example

An Aspen simulation of the process shown in FIG. 1 and described above was carried out using an appropriate data deck. In this case a solvent system of 1:1:1 NBA:1,4-BDO:THF was used in a process for the production of 1,4-BDO and THF from furan. In this process, furan was contacted with hydrogen and water in a reactor in the presence of a catalytic composition and a portion of the furan was converted to 1,4-BDO, NBA and THF. The resultant reactor product stream was subjected to gas liquid separation such that stream 4 had the composition shown in Table 1.

The separation set up shown in FIG. 1 was applied and the resultant isolated product stream compositions are also shown in Table 1.

The results demonstrate a facile separation system in which the three products can each be isolated separately in a pure stream. Only a portion of the THF, 1,4-BDO and NBA present need to be isolated, with the rest recycled and re-used. This allows a much less complex set up and a much reduced distillation duty for this system compared with a process in which a solvent not selected from NBA, THF and/or 1,4-BDO is used.

TABLE 1

| | molar ratios | | | |
|---|---|---|---|---|
| | Stream 4 | Stream 18 | Stream 26 | Stream 39 |
| Water | 460 | 0 | 0 | 0 |
| Furan | 15 | 0 | 0 | 0 |
| THF | 107 | 0 | 45 | 0 |
| 1,4-BDO | 107 | 0 | 0 | 43 |
| NBA | 72 | 11 | 0 | 0 |

That which is claimed is:

1. A process for the production of 1,4-BDO and THF from furan, said process comprising:
   (i) contacting furan with hydrogen and water in a reactor in the presence of a catalytic composition, wherein the furan and water are contacted in the presence of a solvent, said solvent comprising THF, 1,4-BDO and NBA, wherein each of THF, 1,4-BDO and NBA are in an amount of at least 10 wt % and no more than 70 wt % and the sum of all does not exceed 100 wt % (based on the solvent), such that a single phase is formed with the solvent, furan and water and converting at least a portion of said furan to 1,4-BDO and THF;
   (ii) producing a reactor product stream comprising gases, water, THF, 1,4-BDO and furan;
   (iii) separating gases from the reactor product stream;
   (iv) then separating at least a portion of each of the THF and 1,4-BDO from said reactor product stream; and
   (v) recycling the remainder of the reactor product stream, comprising water, optionally furan, and more than one of THF, 1,4-BDO and NBA, to the reactor.

2. The process according to claim 1, wherein the reactor product stream also comprises NBA and at least a portion of the NBA is separated from said reactor product stream in step (iv).

3. The process according to claim 1, wherein the portion of each of the THF, 1,4-BDO and NBA separated from the reactor product stream in step iv) corresponds to at least 90 wt % of the amount of each produced in the reaction of the furan with hydrogen and water.

4. The process according to claim 3, wherein the portion of each of the THF, 1,4-BDO and NBA separated from the reactor product stream in step iv) corresponds to at least 100 wt % of the amount of each produced in the reaction of the furan with hydrogen and water.

5. The process according to claim 2, wherein separating at least a portion of each of the THF, 1,4-BDO and NBA from said reactor product stream comprises, in a first step, separating by distillation a bottoms stream comprising water and 1,4-BDO from a top stream comprising THF, NBA and water and, optionally, furan.

6. The process according to claim 5, wherein the stream comprising THF, NBA and water is subjected to liquid/liquid separation to provide an aqueous stream which is recycled to the reactor and an organics stream comprising THF and NBA.

7. The process according to claim 1, wherein the amount of NBA, 1, 4-BDO and THF produced in the reactors is isolated with the remaining amount being recycled.

\* \* \* \* \*